US009399014B2

(12) United States Patent
Tarrago et al.

(10) Patent No.: US 9,399,014 B2
(45) Date of Patent: *Jul. 26, 2016

(54) PHARMACEUTICAL TOPICAL COMPOSITIONS

(71) Applicant: Ferrer Internacional, S.A., Barcelona (ES)

(72) Inventors: Cristina Tarrago, Esplugues del Llobregat (ES); Benjamin Santos, Barcelona (ES); Manuel Raga, Barcelona (ES); Antonio Guglietta, Molins de Rei (ES)

(73) Assignee: FERRER INTERNACIONAL, S.A., Barcelona (ES)

( * ) Notice: Subject to any disclaimer, the term of this patent is extended or adjusted under 35 U.S.C. 154(b) by 60 days.

This patent is subject to a terminal disclaimer.

(21) Appl. No.: 14/197,933

(22) Filed: Mar. 5, 2014

(65) Prior Publication Data

US 2014/0187578 A1    Jul. 3, 2014

Related U.S. Application Data

(62) Division of application No. 13/124,403, filed as application No. PCT/EP2009/063625 on Oct. 16, 2009.

(30) Foreign Application Priority Data

Oct. 17, 2008   (EP) .................................. 08166933

(51) Int. Cl.
| | | |
|---|---|---|
| *A01N 43/42* | (2006.01) | |
| *A61K 31/47* | (2006.01) | |
| *A61K 9/06* | (2006.01) | |
| *A61K 9/00* | (2006.01) | |
| *A61K 47/06* | (2006.01) | |
| *A61K 31/4709* | (2006.01) | |
| *A61K 47/10* | (2006.01) | |
| *A61K 47/12* | (2006.01) | |
| *A61K 47/14* | (2006.01) | |
| *A61K 47/44* | (2006.01) | |

(52) U.S. Cl.
CPC ................. *A61K 9/06* (2013.01); *A61K 9/0014* (2013.01); *A61K 31/4709* (2013.01); *A61K 47/06* (2013.01); *A61K 47/10* (2013.01); *A61K 47/12* (2013.01); *A61K 47/14* (2013.01); *A61K 47/44* (2013.01)

(58) Field of Classification Search
CPC ... A61K 31/4709; A61K 47/06; A61K 47/10; A61K 47/12; A61K 47/14; A61K 47/44; A61K 9/0014; A61K 9/06
USPC ................................................. 514/312, 314
See application file for complete search history.

(56) References Cited

U.S. PATENT DOCUMENTS 6,335,447 B1     1/2002  Hayashi et al.
2008/0166398 A1*  7/2008  Palacin ................ A61K 9/0014
                                                      424/450

FOREIGN PATENT DOCUMENTS

| EP | 1 698 336 A1 | 9/2006 |
| EP | 1 941 880 A1 | 7/2008 |
| JP | 2002-356426 A | 12/2002 |
| WO | WO 2006/092374 | * 9/2006 |

OTHER PUBLICATIONS

Kadono et al. , 2002, JP 2002-356426, (English translation).*
Abhijit A. Date et al; A review of nanotechnological approaches for the prophylaxis of HIV/AIDS; Biomaterials; No. 34; 2013; pp. 6202-6228.
B. Santos et al.; Preclinical in Vitro and in Vivo Absorption Evaluation of Ozenoxacin (GF-001001-00): A Novel Topical Non-Fluorinated Quinolone; Program and Abstracts of the Interscience Conference on Antimicrobial Agents and Chemotherapy; Washington, D.C. vol. 47; Sep. 20, 1997; p. 26.
Bonatti, US Infectious Disease, 2009, 48-51.
C. Tarrago et al.; Ozenoxacin (gf-001001-00): In vitro antibacterial activity compared with other antibacterial agents agains clinical isolates from wound infections and selection of resistant mutants; Program and abstracts of the Interscience Conference on Antimicrobial Agents and Chemotherapy; Washington DC; vol. 47; Sep. 20, 2007; p. 259-260.
Hugo Bonatti et al.; Best Practices in the Treatment of Complicated Skin and Skin Structure Infections Due to Methicillin-resistant *Staphylococcus aureus*; US Infectious Disease; 2009; pp. 48-51.
International Preliminary Report on Patentability (Form PCT/IPEA/409 issued in PCT/EP2009/06325 on Apr. 6, 2010).
International Search Report (Form PCT/ISA/210 issued in PCT/EP2009/063625 on Apr. 6, 2010).
Masanori Kakuno et al.; Skin compositions containing pyridonecarboxylate derivatives; XP002513715; retrieved from STN Database accession 2002:944683.
Notice of Allowability dated Jan. 10, 2014 in U.S. Appl. No. 13/124,403.
Sexually transmitted infections (STIs); World Health Organization fact sheet (http://www.who.int/mediacentre factsheets/fs110/en/; May 2013.
Tetsumi Yamakawa; In vitro and in vivo antibacterial activity of T-3912, a novel non-fluorinated topical quinolone; Journal of Antimicrobial Chemotherapy; vol. 49; No. 3; pp. 455-465; Mar. 2002.
The American College of Obstetricians and Gynecologists FAQ document (2009).
U.S. Non-Final Office Action dated Sep. 9, 2013 in U.S. Appl. No. 13/124,403.
Written Opinion of the International Searching Authority (Form PCT/ISA/237 issued in PCT/EP2009063625 on Apr. 6, 2010).

* cited by examiner

*Primary Examiner* — Uma Ramachandran
(74) *Attorney, Agent, or Firm* — Birch, Stewart, Kolasch & Birch, LLP

(57) ABSTRACT

The invention provides pharmaceutical stable semisolid topical compositions comprising between 0.2 to 5% of a desfluoroquinolone compound, and a suitable carrier to manufacture an ointment or a cream.

2 Claims, No Drawings

PHARMACEUTICAL TOPICAL COMPOSITIONS

This application is a Divisional application of U.S. patent application Ser. No. 13/124,403, filed Jul. 12, 2011, which is the U.S. National Phase of PCT/EP2009/063625, filed Oct. 16, 2009. This application claims priority under 35 U.S.C. §119(a) to European Patent Application No. 08166933.5, filed in Europe on Oct. 17, 2008, the entire contents of which are hereby incorporated by reference.

DESCRIPTION

The present invention concerns topical compositions which comprise a des-fluoroquinolone compound.

Despite advances in antimicrobial therapy over the last 20 years, the incidence of infections caused by multi-drug resistant Gram-positive organisms, which are major pathogens in primary uncomplicated skin and skin structure infections (impetigo, foliculitis, forunculosis, acne, secondarily-infected traumatic lesions, overinfected dermatoses, and secondarily-infected burns) has been increasing. Recently, the increase of community-adquired methicillin-resistant *Staphylococcus aureus* (MRSA) infections and the emergence of plasmid-mediated mupirocin resistance also in MRSA have been reported. Ozenoxacin is a novel non-fluorinated quinolone compound which has shown a high level of activity against Gram-positive organisms, including common quinolone-resistant bacteria. Ozenoxacin, due to its dual target mechanism of action, is active against some resistant mutant strains. Thus, ozenoxacin is a good antibacterial agent candidate to circumvent the current mechanisms of resistance to antibiotics because of its great activity against resistant Gram-positive bacteria.

Ozenoxacin is active against a great number of pathogens, such as *Propionibacterium acnes, Staphylococcus aureus*, methicillin-susceptible *Staphylococcus aureus* (MSSA), methicillin-resistant *Staphylococcus aureus* (MRSA) including ciprofloxacin-resistant strains, methicillin-susceptible *Staphylococcus epidermidis* (MSSE), methicillin-resistant *Staphylococcus epidermidis* (MRSE), *Streptococcus pyogenes*, Group G Streptococci, penicillin-resistant *Streptococcus pneumoniae*, Beta-lactamase positive *Haemophilus influenzae*, non-typeable strains of *Haemophilus influenzae*, Beta-lactamase positive *Moraxella catarrhalis, Neisseria meningitides, Legionella pneumophila, Mycoplasma pneumoniae, Legionella pneumophila, Mycobacterium tuberculosis, Streptococcus agalactiae* group B, *Neisseria gonorrhoeae, Chlamydia trachomatis, Mycoplasma hominis, Ureaplasma urealyticum Helicobacter pylori, Bacteroides fragilis, Clostridium perfringens, Escherichia coli*, quinolone-resistant *Escherichia coli, Salmonella* spp., *Shigella* spp., ciprofloxacin-susceptible *Pseudomonas aeruginosa, Clostridium difficile*, and *Listeria monocytogenes*.

Ozenoxacin (I) was firstly disclosed in U.S. Pat. No. 6,335,447, and equivalent patents. Its chemical name is 1-cyclopropyl-8-methyl-7-[5-methyl-6-(methylamino)-3-pyridinyl]-4-oxo-1,4-dihydro-3-quinolinecarboxylic acid. Its chemical formula is:

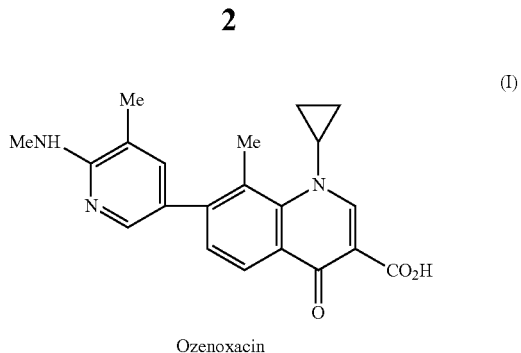

Ozenoxacin

Topical application of antimicrobial agents is a useful tool for therapy of skin and skin structures infections, sexually transmitted diseases and genital tract infections and some systemic infections susceptible to topical treatment. Topical antimicrobial therapy has several potential advantages compared with systemic therapy. Firstly, it can avoid an unnecessary exposure of the gut flora which may exert selection for resistance. Secondly, it is expected that the high local drug concentration in topical application and the negligible systemic absorption should overwhelm many mutational resistances. Thirdly, topical applications are less likely than systemic therapy to cause side effects. Accordingly, some topical compositions comprising ozenoxacin have been reported in the art.

JP2002356426A discloses ointments and gels for skin. An ointment comprising ozenoxacin 1%, N-methyl-2-pyrrolidone 8%, propylene glycol 14.9%, oleic acid 0.9%, diisopropanolamine 2.3%, polyethylene glycol 400 20.2%, polyethylene glycol 4000 50.2%, and water 3.2% is reported in Example 2.

JP2003226643A discloses aqueous solutions comprising ozenoxacin, cyclodextrin, and a viscous agent.

EP1731138A1 discloses fine particle dispersion liquid comprising ozenoxacin to be used in the manufacture of pharmaceutical compositions.

WO2007015453A1 discloses lotions comprising ozenoxacin.

JP2007119456A discloses aqueous suspensions containing nanoparticles and solution granules of ozenoxacin to be used in the manufacture of pharmaceutical compositions. Ophthalmic solutions are mentioned preferably.

A combined use of ozenoxacin, magnesium ions, and hydroxypropyl-β-cyclodextrin specially for ophthalmic use is disclosed in Yamakawa, T. et al., *Journal of Controlled Release* (2003), 86(1), 101-103.

Semisolid topical compositions are useful alternatives to liquid compositions, because of their better manipulation and consequent patient preferences. However, in spite of the great diversity of components present in the semisolid compositions disclosed in the art, no quantitative stability studies are available for them. Thus, there is a need of proved stable semisolid topical compositions comprising ozenoxacin as active ingredient, wherein microbiological and therapeutic activities are warranted because of demonstrated durable and prolonged pharmaceutical stability.

Accordingly, an object of the present invention relates to pharmaceutical stable semisolid topical compositions comprising between 0.2 to 5% of the composition of ozenoxacin, and a suitable carrier to manufacture an ointment or a cream. Preferably, the amount of ozenoxacin is from 0.5% to 2%, and more preferably is 1%. In the present invention all percentages are expressed in weight percent unless otherwise specified.

According to the present invention, an ointment wherein the suitable carrier is selected from white wax, white soft paraffin, and mixtures thereof, is provided. White soft paraffin is preferred.

According to the present invention, a cream wherein the suitable carrier comprises a mixture of emulsifiers, surfactants, oil components, low melting point waxes, water, water dispersible components, and non-formaldehyde-donating preservatives, is provided.

Accordingly, the present invention provides a cream comprising
a) 0.2-5% of ozenoxacin, and
b) a suitable carrier comprising:
b.1) 15-25% of one or more emulsifiers;
b.2) 10-20% of one or more surfactants;
b.3) 5-15% of an oil component;
b.4) 1-10% of one or more low melting point waxes selected from fatty acids having 8 to 30 carbon atoms, fatty alcohols having 8 to 30 carbon atoms, fatty acid esters having 8 to 30 carbon atoms, fatty acid amides having 8 to 30 carbon atoms, silicone waxes, and mixtures thereof;
b.5) water;
b.6) 10-20% of one or more water dispersible components selected from polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide, and mixtures thereof; and
b.7) 0.01-1% of one or more non-formaldehyde-donating preservatives;
wherein the amount of component b.5 is an amount to complete 100 percent by weight of the composition and all percentages being weight percent and based on the total weight of the composition.

According to an embodiment, the present invention provides a cream wherein the carrier comprises:
18 to 22% of component b.1;
13 to 15% of component b.2;
7 to 9% of component b.3;
3 to 5% of component b.4;
component b.5;
13 to 17% of component b.6;
0.05 to 0.15% of component b.7;
wherein the amount of component b.5 is an amount to complete 100 percent by weight of the composition.

According to a further embodiment, the present invention provides a cream wherein the carrier comprises:
20% of component b.1;
14% of component b.2;
8% of component b.3;
4% of component b.4;
component b.5;
15% of component b.6;
0.1% of component b.7;
wherein the amount of component b.5 is an amount to complete 100 percent by weight of the composition.

According to a further embodiment, the amount of water in the carrier is 30 to 45% by weight.

In the present invention the emulsifiers are selected from ethylene glycol monostearate, sorbitan tristearate, a mixture of PEG6 stearate, glycol stearate and PEG32 stearate, and hydrogenated lecithin, and mixtures thereof, preferably the emulsifiers are a mixture of PEG6 stearate, glycol stearate and PEG32 stearate.

In the present invention the surfactants are selected from sorbitan oleate monoolein/propylene glycol, $C_8/C_{10}$ fatty acid mono- and diglycerides from coconut oil, soy lecithin, egg phosphatides, citric acid esters of monoglycerides, lactic acid esters of monoglycerides, diacetyl tartaric acid esters of monoglycerides, succinic acid esters of monoglycerides, sucrose fatty acid esters, polyglycolyzed glycerides of oleic acids, polyglycolyzed glycerides of linoleic acid, polyglycerol esters of fatty acids, including both long chain and medium chain fatty acids, and polyglyceryl esters of mixed fatty acids, and mixtures thereof. Preferably, the surfactants are polyglycolyzed glycerides of oleic acids.

In the present invention the oil components are selected from Guerbet alcohols based on fatty alcohols containing 8 to 10 carbon atoms, esters of linear $C_{6-22}$ fatty acids with linear or branched $C_{6-22}$ fatty alcohols, esters of branched $C_{6-13}$ carboxylic acids with linear or branched $C_{6-22}$ fatty alcohols, esters of linear $C_{6-22}$ fatty acids with 2-ethyl hexanol, esters of $C_{3-38}$ alkylhydroxycarboxylic acids with linear or branched $C_{6-22}$ fatty alcohols, esters of linear or branched fatty acids with polyhydric alcohols or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols or Guerbet alcohols with benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates based on fatty alcohols containing 8 to 10 carbon atoms, esters of benzoic acid with linear or branched $C_{6-22}$ alcohols, linear or branched, symmetrical or nonsymmetrical dialkyl ethers containing 6 to 22 carbon atoms per alkyl group, ring opening products of epoxidized fatty acid esters with polyols, silicone oils, and aliphatic or naphthenic hydrocarbons, and mixtures thereof. Preferably, the oil components are Guerbet alcohols based on fatty alcohols containing 8 to 10 carbon atoms, such as 2-octyl dodecanol (Eutanol® G PH).

Because they are primary, branched, and of high molecular weight, Guerbet alcohols have low irritation potential, are liquid to extremely low temperatures, are low in volatility, are useful as superfatting agents and are good lubricants.

In the present invention the low melting point waxes are selected from fatty acids having 8 to 30 carbon atoms, fatty alcohols having 8 to 30 carbon atoms, fatty acid esters having 8 to 30 carbon atoms, fatty acid amides having 8 to 30 carbon atoms, silicone waxes, and mixtures thereof. Preferably, the low melting point waxes are fatty alcohols having 8 to 30 carbon atoms. More preferably, stearyl alcohol is selected from fatty alcohols.

On account of its consistency giving characteristics, stearyl alcohol acts as a convenient viscosity regulator.

In the present invention the water dispersible components are selected from polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide, and mixtures thereof. Preferably, the water dispersible component is propylene glycol.

In the present invention the non-formaldehyde-donating preservatives are selected from ammonium benzoate, ammonium propionate, benzisothiazolinone, benzoic acid, benzotriazole, benzyl alcohol, benzylparaben, 5-bromo-5-nitro-1,3-dioxane, 2-bromo-2-nitropropane-1,3-diol, butyl benzoate, butylparaben, calcium benzoate, calcium paraben, calcium propionate, calcium salicylate, calcium sorbate, chlorhexidine diacetate, chlorhexidine digluconate, chlorhexidine dihydrochloride, chloroacetamide, chlorobutanol, p-chlorom-cresol, chlorophene, p-chlorophenol, chlorophenesin, chlorothymol, chloroxylenol, m-cresol, o-cresol, p-cresol, dehydroacetic acid, dibromopropamidine diisethionate, dimethyl oxazolidine, dithiomethylbenzamide, domiphen, ethyl ferulate, ethylparaben, ferulic acid, glyoxal, hexamidine, hexamidine diparaben, hexamidine paraben, 4-hydroxybenzoic acid, hydroxymethyl dioxoazabicyclooctane, iodopropynyl butylcarbamate, isobutylparaben, isodecylparaben, isopropyl cresols, isopropylparaben, isopropyl sorbate, lauryl diethylenediaminoglycine HCl, magnesium benzoate, magnesium propionate, methyl-chloroisothiazolinone, methylparaben, octylisothiazolinone, panthenyl ethyl ether benzoate, phenethyl alcohol, phenol, phenoxyethanol, phenoxyethylparaben, phenoxyisopropanol, phenyl benzoate, phenylparaben, o-phenylphenol, polymethoxy bicyclic oxazolidine, potassium benzoate, potassium butylparaben, potassium ethylparaben, potassium methylparaben, potassium paraben, potassium phenoxide, potassium propionate, potassium propylparaben, potassium sorbate, propionic acid, propyl benzoate, propylparaben, quaternium-8 (methyl and stearyl dimethylaminoethyl methacrylate quaternized with dimethyl sulfate), quaternium-14 (ethanaminium, N,N,N-trimethyl-2-[(2-methyl-1-oxo-2-propenyl)oxy]-, methyl sulfate, homopolymer), quaternium-15 (ethanaminium, N,N,N-trimethyl-2-[(2-methyl-1-oxo-2-propenyl)oxy]-chloride, polymer with 2-propenamide), sodium benzoate, sodium butylparaben, sodium p-chloro-m-cresol, sodium dehydroacetate, sodium ethylparaben, sodium formate, sodium hydroxymethane sulfonate, sodium hydroxymethylglycinate, sodium isobutylparaben, sodium isopropylparaben, sodium lauryl diethylenediaminoglycinate, sodium methylparaben, sodium paraben, sodium phenylsulfonate, sodium phenoxide, sodium o-phenylphenate, sodium propionate, sodium propylparaben, sodium sorbate, sorbic acid, TEA-sorbate (triethanolamine sorbate), thianthol (2,7-dimethylthianthrene), triclocarban, triclosan, and undecylenoyl PEG5 paraben (ester of undecylenic acid and PEG5 paraben), and mixtures thereof. Preferably, the non-formaldehyde-donating preservative is benzoic acid.

Another object of the present invention is the use of the compositions of the present invention in the treatment or prevention of skin and skin structure infections in a human or an animal. Accordingly, the present invention provides the use of ointments and creams of the present invention in the treatment or prevention of skin and skin structure infections, being non-limitative examples of such skin and skin structure infections impetigo, foliculitis, forunculosis, acne, secondarily-infected traumatic lesions, overinfected dermatoses, and secondarily-infected burns, and those skin and skin structure infections caused by methicillin-susceptible *Staphylococcus aureus* (MSSA), methicillin-resistant *Staphylococcus aureus* (MRSA) including ciprofloxacin-resistant strains, methicillin-susceptible *Staphylococcus epidermidis* (MSSE), methicillin-resistant *Staphylococcus epidermidis* (MRSE), *Streptococcus pyogenes*, and Group G Streptococci.

Another object of the present invention is the use of new compositions in the treatment or prevention of sexually transmitted diseases and genital tract infections in a human or an animal. Accordingly, the present invention provides the use of ointments and creams of the present invention in the treatment or prevention of sexually transmitted diseases and genital tract infections, such as those caused by *Streptococcus agalactiae* group B, *Neisseria gonorrhoeae*, *Chlamydia trachomatis*, *Mycoplasma hominis*, and *Ureaplasma urealyticum*.

Another object of the present invention is the use of new compositions in the eradication of nasopharynx infections in asymptomatic nasal carriers in a human or an animal. Accordingly, the present invention provides the use of ointments and creams of the present invention in the eradication of nasopharynx infections in asymptomatic nasal carriers, the infections being caused by methicillin-susceptible *Staphylococcus aureus* (MSSA), methicillin-resistant *Staphylococcus aureus* (MRSA) including ciprofloxacin-resistant strains, penicillin-resistant *Streptococcus pneumoniae*, Beta-lactamase positive *Haemophilus influenzae*, non-typeable strains of *Haemophilus influenzae*, Beta-lactamase positive *Moraxella catarrhalis, Neisseria meningitides, Legionella pneumophila, Mycoplasma pneumoniae, Legionella pneumophila*, and *Mycobacterium tuberculosis*.

The compositions of the present invention may be used by direct application to the affected or to protect skin or genital area. Also the compositions may be used by administration to the nasal cavity, preferably to the nasopharynx, in particular the anterior nasopharynx.

Also, the compositions of the present invention may be used in the treatment of skin and skin structure infections, sexually transmitted diseases and genital tract infections, and in the eradication of nasopharynx infections in asymptomatic nasal carriers when such infections are resistant to usual topical antibiotics, being such antibiotics mupirocin, fusidic acid, retapamulin, and quinolone compounds, i.e. nadifloxacin.

Another object of the present invention is to provide novel methods to treat or prevent skin and skin structure infections in a human or an animal in need by administering the compositions of the present invention.

Another object of the present invention is to provide novel methods to treat or prevent sexually transmitted diseases and genital tract infections in a human or an animal in need by administering the compositions of the present invention.

Another object of the present invention is to provide novel methods for the eradication of nasopharynx infections in asymptomatic nasal carriers in a human or an animal in need by administering the compositions of the present invention.

The compositions according to the invention can be used effectively and safely without clinically significant dermatological or systemic related adverse events, because of the skin absorption of ozenoxacin is negligible.

Throughout the description and claims the word "comprise" and variations of the word, such as "comprising", are not intended to exclude other technical features, additives, components, or steps. Additional objects, advantages and features of the invention will become apparent to those skilled in the art upon examination of the description or may be learned by practice of the invention. The following examples are provided by way of illustration, and are not intended to be limiting of the present invention.

EXAMPLES

Example 1

Ointment Containing 1% of Ozenoxacin a) 100 g Composition

| | |
|---|---|
| Ozenoxacin | 1 g |
| White soft paraffin | 99 g | b) Manufacturing

White soft paraffin (99 parts) was melt to homogeneity at 70-75° C. in a reactor of adequate capacity for the batch manufacturing, equipped with low speed stirring (anchor stirring) and high speed stirring, and a system of heating and cooling. The paraffin was cooled at 50-55° C. Ozenoxacin (1 part) was added and dispersed into paraffin by stirring. The final dispersion was cooled to 25-30° C. A homogeneous, yellow pale, oily-like base ointment was obtained. The final ointment was packed in aluminium 20 mL tubes by using an automatic system.

c) Stability

The inert nature of the soft paraffin carrier warrants that the ointment can be stored stably for 18 months at least.

Example 2

Cream Containing 1% of Ozenoxacin a) 100 g Composition

| | |
|---|---|
| Ozenoxacin | 1 g (1%) |
| PEG6 stearate and glycol stearate and PEG32 stearate (Tefose ® 63) | 20 g (20%) |
| Oleoyl macrogol-6-glycerides (Labrafil ® M1944 CS) | 14 g (14%) |
| 2-Octyl dodecanol (Eutanol ® G PH) | 8 g (8%) |
| Stearyl alcohol (Lanette ® 18) | 4 g (4%) |
| Propylene glycol | 15 g (15%) |
| Benzoic acid | 0.1 g (0.1%) |
| Purified water | 37.9 g (37.9%) | b) Manufacturing

1. Propylene glycol (15 parts) and water (37.9 parts) were added to a semisolid reactor of adequate capacity.
2. The mixture was heated at 70-75° C. under slow speed stirring.
3. A mixture of Tefose® 63 (20 parts), Labrafil® M 1944 CS (14 parts), Lanette® 18 (4 parts), and benzoic acid (0.1 parts) was melt at 70-75° C. in a glass/aluminium beaker of adequate capacity under low speed stirring.
4. Final mixture of step 3 (organic phase) was added to the semisolid reactor. The mixture was stirred at low speed with an anchor stirring and at high speed with a high shear mixer for 5 minutes.
5. A mixture of Eutanol® G PH (8 parts) and ozenoxacin (1 parts) was added to a glass beaker of adequate capacity provided with an adequate stirrer. The mixture was heated at 50-55° C. under stirring.
6. The suspension of step 5 was added to the emulsion of step 4 and stirred at low speed with the anchor stirring and at high speed with a high shear mixer for 20 minutes.
7. The temperature of the resulting cream was let down to 25-30° C. by stopping the heating. Bulk homogeneity was checked.
8. The final cream was packed into aluminium 20 mL tubes with high density polyethylene cap by using an automatic system.

c) Stability

Tables 1-12 summarize the stability studies performed with some development batches.

TABLE 1

Batch size: 600 g
Experimental conditions: 25 ± 2° C./60% ± 5% RH (1)

| | Initial | t = 6 months |
|---|---|---|
| Appearance | Conforms | Conforms |
| Active ingredient assay (%; mean) | 100.91 | 100.61 |
| Impurities assay (%)   Unknown impurities | n.d. (2) | n.d. |
| Total impurities | n.d. | n.d. |
| Degradation products assay (%) | n.d. | n.d. |
| Benzoic acid assay (%, mean) | 102.14 | 105.65 |
| Particle size (D 90, microns) | 4.44 | 3.90 |
| Viscosity (cPs) | 300406 | 212344 |
| pH | 3.97 | 3.99 |

(1) Relative Humidity ; (2) Not detected

TABLE 2

Batch size: 600 g
Experimental conditions: 30 ± 2° C./65% ± 5% RH

| | Initial | t = 6 months |
|---|---|---|
| Appearance | Conforms | Conforms |
| Active ingredient assay (%; mean) | 100.91 | 100.96 |
| Impurities assay (%)   Unknown impurities | n.d. | n.d. |
| Total impurities | n.d. | n.d. |
| Degradation products assay (%) | n.d. | n.d. |
| Benzoic acid assay (%, mean) | 102.14 | 108.76 |
| Particle size (D 90, microns) | 4.44 | 5.46 |
| Viscosity (cPs) | 300406 | 304312 |
| pH | 3.97 | 3.89 |

TABLE 3

Batch size: 600 g
Experimental conditions: 40 ± 2° C./75% ± 5% RH

| | Initial | t = 1 month | t = 3 months | t = 6 months |
|---|---|---|---|---|
| Appearance | Conforms | Conforms | Conforms | Conforms |
| Active ingredient assay (%; mean) | 100.91 | 99.14 | 100.85 | 99.73 |
| Impurities assay (%)   Unknown impurities | n.d. | n.d. | n.d. | n.d. |
| Total impurities | n.d. | n.d. | n.d. | n.d. |
| Degradation products assay (%) | n.d. | n.d. | n.d. | n.d. |
| Benzoic acid assay (%, mean) | 102.14 | 100.12 | 102.65 | 108.75 |
| Particle size (D 90, microns) | 4.44 | 5.30 | 5.97 | 9.64 |
| Viscosity (cPs) | 300406 | 360031 | 280969 | 398719 |
| pH | 3.97 | 3.91 | 4.10 | 3.89 |

TABLE 4

Batch size: 600 g
Experimental conditions: 25 ± 2° C./ 60% ± 5% RH

|  | Initial | t = 6 months |
|---|---|---|
| Appearance | Conforms | Conforms |
| Active ingredient assay (%; mean) | 101.33 | 100.81 |
| Impurities assay (%) Unknown impurities | n.d. | n.d. |
| Total impurities | n.d. | n.d. |
| Degradation products assay (%) | n.d. | n.d. |
| Benzoic acid assay (%, mean) | 103.85 | 109.0 |
| Particle size (D 90, microns) | 4.18 | 3.88 |
| Viscosity (cPs) | 498375 | 395062 |
| pH | 4.04 | 4.18 |

TABLE 5

Batch size: 600 g
Experimental conditions: 30 ± 2° C./ 65% ± 5% RH

|  | Initial | t = 6 months |
|---|---|---|
| Appearance | Conforms | Conforms |
| Active ingredient assay (%; mean) | 101.33 | 100.41 |
| Impurities assay (%) Unknown impurities | n.d. | n.d. |
| Total impurities | n.d. | n.d. |
| Degradation products assay (%) | n.d. | n.d. |
| Benzoic acid assay (%, mean) | 103.85 | 110.03 |
| Particle size (D 90, microns) | 4.18 | 5.01 |
| Viscosity (cPs) | 498375 | 498156 |
| pH | 4.04 | 4.22 |

TABLE 6

Batch size: 600 g
Experimental conditions: 40 ± 2° C./ 75% ± 5% RH

|  | Initial | t = 1 month | t = 3 months | t = 6 months |
|---|---|---|---|---|
| Appearance | Conforms | Conforms | Conforms | Conforms |
| Active ingredient assay (%; mean) | 101.33 | 99.82 | 101.22 | 100.56 |
| Impurities assay (%) Unknown impurities | n.d. | n.d. | n.d. | n.d. |
| Total impurities | n.d. | n.d. | n.d. | n.d. |
| Degradation products assay (%) | n.d. | n.d. | n.d. | n.d. |
| Benzoic acid assay (%, mean) | 103.85 | 103.22 | 107.47 | 111.47 |
| Particle size (D 90, microns) | 4.18 | 4.93 | 6.0 | 7.86 |
| Viscosity (cPs) | 498375 | 555500 | 324719 | 506062 |
| pH | 4.04 | 3.93 | 3.93 | 4.06 |

TABLE 7

Batch size: 8 Kg
Experimental conditions: 25 ± 2° C./ 60% ± 5% RH

|  | Initial | t = 3 months | t = 6 months | t = 12 months |
|---|---|---|---|---|
| Appearance | Conforms | Conforms | Conforms | Conforms |
| Active ingredient assay (%; mean) | 102.16 | 103.38 | 101.79 | 99.98 |
| Impurities assay (%) Unknown impurities | n.d. | n.d. | n.d. | n.d. |
| Total impurities | n.d. | n.d. | n.d. | n.d. |
| Degradation products assay (%) | n.d. | n.d. | n.d. | n.d. |
| Benzoic acid assay (%, mean) | 100.59 | 100.20 | 103.71 | 102.54 |
| Particle size (D 90, microns) | 5.85 | 6.02 | 3.64 | 2.89 |
| Viscosity (cPs) | 400234 | 209531 | 320094 | 384188 |
| pH | 4.18 | 4.42 | 4.21 | 4.05 |

TABLE 8

Batch size: 8 Kg
Experimental conditions: 30 ± 2° C./ 65% ± 5% RH

|  | Initial | t = 1 month | t = 3 months | t = 6 months | t = 12 months |
|---|---|---|---|---|---|
| Appearance | Conforms | Conforms | Conforms | Conforms | Conforms |
| Active ingredient assay (%; mean) | 102.16 | 101.67 | 103.12 | 102.92 | 98.98 |
| Impurities assay (%) Unknown Impurities | n.d. | n.d. | n.d. | n.d. | n.d. |
| Total Impurities | n.d. | n.d. | n.d. | n.d. | n.d. |
| Degradation products assay (%) | n.d. | n.d. | n.d. | n.d. | n.d. |
| Benzoic acid assay (%, mean) | 100.59 | 99.70 | 101.38 | 105.21 | 103.26 |
| Particle size (D 90, microns) | 5.85 | 5.5 | 5.03 | 3.68 | 3.79 |
| Viscosity (cPs) | 400234 | 350875 | 224031 | 334219 | 338812 |
| pH | 4.18 | 3.95 | 4.05 | 3.95 | 4.04 |

TABLE 9

| Batch size: 8 Kg Experimental conditions: 40 ± 2° C./ 75% ± 5% RH | Initial | t = 1 month | t = 3 months | t = 6 months |
|---|---|---|---|---|
| Appearance | Conforms | Conforms | Conforms | Conforms |
| Active ingredient assay (%; mean) | 102.16 | 100.17 | 102.89 | 102.43 |
| Impurities assay (%) Unknown impurities | n.d. | n.d. | n.d. | n.d. |
| Total impurities | n.d. | n.d. | n.d. | n.d. |
| Degradation products assay (%) | n.d. | n.d. | n.d. | n.d. |
| Benzoic acid assay (%, mean) | 100.59 | 103.35 | 102.28 | 103.21 |
| Particle size (D 90, microns) | 5.85 | 8.27 | 5.96 | 3.56 |
| Viscosity (cPs) | 400234 | 439250 | 308437 | 328562 |
| pH | 4.18 | 3.97 | 3.99 | 3.83 |

TABLE 10

| Batch size: 8 Kg Experimental conditions: 25 ± 2° C./ 60% ± 5% RH | Initial | t = 3 months | t = 6 months | t = 12 months |
|---|---|---|---|---|
| Appearance | Conforms | Conforms | Conforms | Conforms |
| Active ingredient assay (%; mean) | 99.70 | 102.59 | 100.45 | 99.30 |
| Impurities assay (%) Unknown impurities | n.d. | n.d. | n.d. | n.d. |
| Total impurities | n.d. | n.d. | n.d. | n.d. |
| Degradation products assay (%) | n.d. | n.d. | n.d. | n.d. |
| Benzoic acid assay (%, mean) | 102.72 | 101.14 | 103.71 | 103.06 |
| Particle size (D 90, microns) | 4.68 | 5.96 | 2.97 | 2.41 |
| Viscosity (cPs) | 309312 | 264656 | 247500 | 317875 |
| pH | 4.30 | 4.38 | 3.89 | 4.29 |

TABLE 11

| Batch size: 8 Kg Experimental conditions: 30 ± 2° C./ 65% ± 5% RH | Initial | t = 1 month | t = 3 months | t = 6 months | t = 12 months |
|---|---|---|---|---|---|
| Appearance | Conforms | Conforms | Conforms | Conforms | Conforms |
| Active ingredient assay (%; mean) | 99.70 | 100.65 | 102.37 | 100.90 | 99.54 |
| Impurities assay (%) Unknown Impurities | n.d. | n.d. | n.d. | n.d. | n.d. |
| Total Impurities | n.d. | n.d. | n.d. | n.d. | n.d. |
| Degradation products assay (%) | n.d. | n.d. | n.d. | n.d. | n.d. |
| Benzoic acid assay (%, mean) | 102.72 | 102.0 | 102.11 | 104.11 | 103.78 |
| Particle size (D 90, microns) | 4.68 | 6.46 | 5.30 | 4.61 | 4.02 |
| Viscosity (cPs) | 309312 | 321250 | 257843 | 304437 | 340750 |
| pH | 4.30 | 3.98 | 4.10 | 3.89 | 4.02 |

TABLE 12

| Batch size: 8 Kg Experimental conditions: 40 ± 2° C./ 75% ± 5% RH | Initial | t = 1 month | t = 3 months | t = 6 months |
|---|---|---|---|---|
| Appearance | Conforms | Conforms | Conforms | Conforms |
| Active ingredient assay (%; mean) | 99.70 | 100.68 | 102.94 | 101.58 |
| Impurities assay (%) Unknown impurities | n.d. | n.d. | n.d. | n.d. |
| Total impurities | n.d. | n.d. | n.d. | n.d. |
| Degradation products assay (%) | n.d. | n.d. | n.d. | n.d. |
| Benzoic acid assay (%, mean) | 102.72 | 102.98 | 103.09 | 104.75 |
| Particle size (D 90, microns) | 4.68 | 6.67 | 4.82 | 3.86 |
| Viscosity (cPs) | 309312 | 400937 | 303625 | 310844 |
| pH | 4.30 | 3.97 | 4.02 | 3.86 |

Example 3

Antibacterial Activity of the Ointment Containing 1% of Ozenoxacin a) Experimental Procedure The antibacterial activity was evaluated in a model of infection consisting of a cutaneous wound infected by *Staphylococcus aureus* (ATCC 6538) in mice after topical administration of the ointment of Example 1.

CD-1 male mice (45 animals) with a body weight of 22-27 g at start of treatment were housed in standard laboratory conditions (temperature 22±1° C. and relative humidity 65±10%; 12-hour light (7:00 am to 7:00 pm)/12-hour dark cycle).

In order to infect the suture threads, they were submerged for 30 minutes in one-night broth of *S. aureus* at a concentration of $10^8$ CFU/mL, previously adjusted by spectrophotometry.

The threads were removed and left to dry on filter paper. Two 1 cm lengths were cut from each suture thread and each length was vortexed in a tube with 1 mL of 0.2% yeast extract. Dilutions were made of these broths and transferred, in duplicate and in parallel, to Cystine-Lactose-Electrolyte-Deficient (CLED) agar in order to find out the concentration on the suture threads. The remainder of the suture thread was kept in a refrigerator until it was used.

The day before the start of the experiment, the animals were shaved and depilated with a commercial depilatory cream.

The mice were allocated at random to three groups consisting of 15 animals. Groups were coded to allow a blind treatment, according to Table 13.

TABLE 13

| # | Group | Treatment | Concentration | Form |
|---|---|---|---|---|
| 1 | A | Placebo | | Ointment |
| 2 | B | Mupirocin | 2% | Ointment |
| 3 | C | Ozenoxacin | 1% | Ointment |

On day 1, at the start of the experiment, the animals were anaesthetized with isoflurane. The infection was induced with a needle threaded with silk suture thread, previously infected with an inoculum of *S. aureus* at a determined concentration. A puncture was made in order that only pierced the skin at the height of the shoulder girdle and exited approximately 1 cm below.

Knots were tied at each end of the thread to ensure that it did not move from its subcutaneous position. Then, a superficial incision was made with a scalpel between both knots, without reaching the *panniculus carnosus*.

The different treatments were applied one and eight hours after the infection. The treatments were applied topically to the affected area. All the applications were done by massaging the infected area for no less than 30 seconds. The treatments continued for four more days and were applied at 12-hour intervals.

The application volume was 0.1 mL/animal. The placebo was received the vehicle used in the formulation of the test item as ointment. The treatments will be coded before their application.

The animals were weighed and any clinical signs related to the test were noted daily.

On day 6, approximately 16 hours after the application, all the animals were sacrificed by cervical dislocation. An area of skin, approximately 1×2 cm and which included the wound, was removed and weighed. This sample was homogenized in 5 mL of physiological saline. This solution (0.1 mL) and three 1:10 consecutive dilutions of the initial 5-mL solution were placed, in parallel, on plates with CLED agar+50 mM $MgCl_2$. In the mupirocin group, the 50 mM $MgCl_2$ was replaced with 2% activated charcoal. The two types of agar plates were used for the placebo group.

$MgCl_2$ was added to the CLED agar to act as a quinolone chelator in order to inhibit the activity of the antibiotic on the plate, while activated charcoal (2%) was used to avoid carry-over of mupirocin in the skin samples of animals treated with 2% mupirocin ointment.

The homogenized samples were kept in a refrigerator until the final counts had been done, in case the counts had to be repeated.

b) Results

Values on CLED Agar+2% Activated Charcoal

In the placebo group, values of 6.53±0.218 (mean±SEM) for Log(CFU/g skin) were obtained in the counts. Growth was observed in all the plates.

In the 2% mupirocin ointment group, the values for Log (CFU/g skin) were 4.92±0.236. Growth was observed in all plates. Statistically significant differences (Student t test, $p<0.01$) were observed between mupirocin and placebo.

The cure rate for 2% mupirocin ointment was 24% compared to the placebo group.

Values on CLED Agar+50 mM $MgCl_2$

In the placebo group, values of 6.32±0.264 (mean±SEM) for Log(CFU/g skin) were obtained in the counts. Growth was observed in all the plates.

In the 1% ozenoxacin ointment group, the values for Log (CFU/g skin) were 3.56±0.248. Growth was observed in 13 of 15 plates. Statistically significant differences (Student t test, $p<0.01$) were observed between ozenoxacin and placebo.

The cure rate for 1% ozenoxacin ointment was 44% compared to the placebo group.

c) Conclusion

A 5-day administration of the ointment containing ozenoxacin 1% induced a statistically significant and higher decrease in bacterial growth in the experimental model of an infection by *Staphylococcus aureus* in mice than obtained with ointment containing mupirocin 2%. No adverse local effects were observed after application of the treatment.

Example 4

Antibacterial Activity of the Cream Containing 1% of Ozenoxacin a) Experimental Procedure The antibacterial activity of cream of Example 2 was evaluated analogously to Example 3a.

The only differences concern the pharmaceutical forms, which are shown in Table 14.

TABLE 14

| # | Group | Treatment | Concentration | Form |
|---|---|---|---|---|
| 1 | A | Placebo | | Cream |
| 2 | B | Mupirocin | 2% | Ointment |
| 3 | C | Ozenoxacin | 1% | Cream | b) Results
Values on CLED Agar+2% Activated Charcoal

In the placebo group, values of 6.80±0.145 (mean±SEM) for Log(CFU/g skin) were obtained in the counts. Growth was observed in all the plates.

In the 2% mupirocin ointment group, the values for Log (CFU/g skin) were 5.01±0.218. Growth was observed in all plates. Statistically significant differences (Student t test, p<0.01) were observed between mupirocin and placebo.

The cure rate for 2% mupirocin ointment was 26% in the observations compared to the placebo group.

Values on CLED Agar+50 mM $MgCl_2$

In the placebo group, values of 6.67±0.171 (mean±SEM) for Log(CFU/g skin) were obtained in the counts. Growth was observed in all the plates.

In the 1% ozenoxacin cream group, the values for Log (CFU/g skin) were 3.10±0.154. Growth was observed in 13 of 15 plates. Statistically significant differences (Student t test, p<0.01) were observed between ozenoxacin and placebo.

The cure rate for 1')/0 ozenoxacin cream was 54% compared to the placebo group.

c) Conclusions

A 5-day administration of the cream containing ozenoxacin 1% induced a statistically significant and higher decrease in bacterial growth in the experimental model of infection by Staphylococcus aureus in mice than obtained with ointment containing mupirocin 2%. No adverse local effects were observed after application of the treatment.

Example 5

Cream Containing 2% of Ozenoxacin 100 g Composition

| | |
|---|---|
| Ozenoxacin | 2 g (2%) |
| PEG6 stearate and glycol stearate and PEG32 stearate (Tefose ® 63) | 20 g (20%) |
| Oleoyl macrogol-6-glycerides (Labrafil ® M1944 CS) | 14 g (14%) |
| 2-Octyl dodecanol (Eutanol ® G PH) | 8 g (8%) |
| Stearyl alcohol (Lanette ® 18) | 4 g (4%) |
| Propylene glycol | 15 g (15%) |
| Benzoic acid | 0.1 g (0.1%) |
| Purified water | 36.9 g (36.9%) |

The manufacturing process is as for Example 2. Stability results were similar to those obtained for Example 2.

Example 6

Phase I Clinical Trial of Ozenoxacin 2% Cream Formulation

Objectives

The primary objective was to assess the systemic absorption following repeated topical applications of ozenoxacin 2% cream by analysing the pharmacokinetic parameters derived from plasma ozenoxacin concentrations.

The secondary objectives were to assess the safety and tolerability after repeated topical applications of ozenoxacin 2% cream.

Methodology

This is a multiple-dose, double blind, randomized, placebo controlled and 2-way crossover clinical trial. 20 healthy caucasian male volunteers aged 18 to 60 years were included. The dose of administration was 0.5 g ozenoxacin 2% cream/ 90 $cm^2$. Each subject received 3 applications of 0.5 g ozenoxacin 2% cream each day for 6 days and 1 single application of 0.5 g ozenoxacin 2% cream on day 7, or 3 applications of placebo cream for 6 days and 1 single application of placebo cream on day 7 at each period according to a randomization code.

Blood samples for plasma ozenoxacin concentration measurements were collected before the 1st and the 2nd applications on day 1, before the 2nd applications on day 2, before the 1st and 3rd applications on day 3 and day 4, before each application on day 5 and day 6, before application on day 7, and at 0.5, 1, 2, 4, 8, 12, 24, 48 and 72 hours after the day 7 application.

Results

After repeated topical application of 10 mg of ozenoxacin (2% cream) three times daily for seven days, all plasma ozenoxacin concentrations were also below the limit of quantitation. Therefore, no systemic absorption was observed.

After repeated topical applications of ozenoxacin 2% cream, preliminary results showed a good tolerability profile. The most commonly recorded adverse events were application site pruritus, and erythema. No serious adverse events were reported. All adverse events were classified as mild or moderate in intensity.

It can be concluded that ozenoxacin 2% cream is well tolerated and dermal absorption is negligible.

Embodiments of the Invention

1. A pharmaceutical stable semisolid topical composition comprising between 0.2 to 5% of the composition of ozenoxacin, and a suitable carrier to manufacture an ointment or a cream.

2. A composition according to embodiment 1 or 2, wherein the amount of ozenoxacin is from 0.5% to 2%.

3. A composition according to embodiment 2, wherein the amount of ozenoxacin is 1%.

4. An ointment comprising a composition according to any one of embodiments 1 to 3, comprising 0.2 to 5% of ozenoxacin wherein the suitable carrier is selected from white wax, white soft paraffin, and mixtures thereof.

5. An ointment according to embodiment 4, wherein the suitable carrier is white soft paraffin.

6. A cream comprising a composition according to any one of embodiments 1 to 3, wherein the suitable carrier comprises a mixture of emulsifiers, surfactants, oil components, low melting point waxes, water, water dispersible components, and non-formaldehyde-donating preservatives.

7. A cream according to embodiment 6, wherein the carrier includes in the following proportions of the cream:
emulsifiers, 15-25%;
surfactants, 10-20%;
oil components, 5-15%;
low melting point waxes, 1-10%;
water, 30-45%;
water dispersible components, 10-20%; and
non-formaldehyde-donating preservatives, 0.01-1%.

8. A cream according to embodiment 7, wherein the carrier includes in the following proportions of the cream:
emulsifiers, 18-22%;
surfactants, 13-15%;
oil components, 7-9%;
low melting point waxes, 3-5%;
water, 35-40%;
water dispersible components, 13-17%; and
non-formaldehyde-donating preservatives, 0.05-0.15%.

9. A cream according to embodiment 8, wherein the carrier includes in the following proportions of the cream:
emulsifiers, 20%;
surfactants, 14%;
oil components, 8%;
low melting point waxes, 4%;
water, 37.9%;
water dispersible components, 15%; and
non-formaldehyde-donating preservatives, 0.1%.

10. A cream according to any one of embodiments 6 to 9, wherein the emulsifiers are selected from ethylene glycol monostearate, sorbitan tristearate, a mixture of PEG6 stearate, glycol stearate and PEG32 stearate, and hydrogenated lecithin, and mixtures thereof.

11. A cream according to embodiment 10, wherein the emulsifiers are a mixture of PEG6 stearate, glycol stearate and PEG32 stearate.

12. A cream according to any one of embodiments 6 to 11, wherein the surfactants are selected from sorbitan oleate monoolein/propylene glycol, $C_8/C_{10}$ fatty acid mono- and diglycerides from coconut oil, soy lecithin, egg phosphatides, citric acid esters of monoglycerides, lactic acid esters of monoglycerides, diacetyl tartaric acid esters of monoglycerides, succinic acid esters of monoglycerides, sucrose fatty acid esters, polyglycolyzed glycerides of oleic acids, polyglycolyzed glycerides of linoleic acid, polyglycerol esters of fatty acids, including both long chain and medium chain fatty acids, and polyglyceryl esters of mixed fatty acids, and mixtures thereof.

13. A cream according to embodiment 12 wherein the surfactants are polyglycolyzed glycerides of oleic acids.

14. A cream according to any one of embodiments 6 to 13, wherein the oil components are selected from Guerbet alcohols based on fatty alcohols containing 8 to 10 carbon atoms, esters of linear $C_{6-22}$ fatty acids with linear or branched $C_{6-22}$ fatty alcohols, esters of branched $C_{6-13}$ carboxylic acids with linear or branched $C_{6-22}$ fatty alcohols, esters of linear $C_{6-22}$ fatty acids with 2-ethyl hexanol, esters of $C_{3-38}$ alkylhydroxycarboxylic acids with linear or branched $C_{6-22}$ fatty alcohols, esters of linear or branched fatty acids with polyhydric alcohols or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols or Guerbet alcohols with benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates based on fatty alcohols containing 8 to 10 carbon atoms, esters of benzoic acid with linear or branched $C_{6-22}$ alcohols, linear or branched, symmetrical or nonsymmetrical dialkyl ethers containing 6 to 22 carbon atoms per alkyl group, ring opening products of epoxidized fatty acid esters with polyols, silicone oils, and aliphatic or naphthenic hydrocarbons, and mixtures thereof.

15. A cream according to embodiment 14 wherein the oil component is the Guerbet alcohol 2-octyl dodecanol.

16. A cream according to any one of embodiments 6 to 15, wherein the low melting point waxes are selected from fatty acids having 8 to 30 carbon atoms, fatty alcohols having 8 to 30 carbon atoms, fatty acid esters having 8 to 30 carbon atoms, fatty acid amides having 8 to 30 carbon atoms, silicone waxes, and mixtures thereof.

17. A cream according to embodiment 16 wherein low melting point waxes are fatty alcohols having 8 to 30 carbon atoms.

18. A cream according to embodiment 17 wherein stearyl alcohol is selected from fatty alcohols.

19. A cream according to any one of embodiments 6 to 18, wherein the water dispersible components are selected from polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide, and mixtures thereof.

20. A cream according to embodiment 19 the water dispersible component is propylene glycol.

21. A cream according to any one of embodiments 6 to 20, wherein the non-formaldehyde-donating preservatives are selected from ammonium benzoate, ammonium propionate, benzisothiazolinone, benzoic acid, benzotriazole, benzyl alcohol, benzylparaben, 5-bromo-5-nitro-1,3-dioxane, 2-bromo-2-nitropropane-1,3-diol, butyl benzoate, butylparaben, calcium benzoate, calcium paraben, calcium propionate, calcium salicylate, calcium sorbate, chlorhexidine diacetate, chlorhexidine digluconate, chlorhexidine dihydrochloride, chloroacetamide, chlorobutanol, p-chloro-m-cresol, chlorophene, p-chlorophenol, chlorophenesin, chlorothymol, chloroxylenol, m-cresol, o-cresol, p-cresol, dehydroacetic acid, dibromopropamidine diisethionate, dimethyl oxazolidine, dithiomethylbenzamide, domiphen, ethyl ferulate, ethylparaben, ferulic acid, glyoxal, hexamidine, hexamidine diparaben, hexamidine paraben, 4-hydroxybenzoic acid, hydroxymethyl dioxoazabicyclooctane, iodopropynyl butylcarbamate, isobutylparaben, isodecylparaben, isopropyl cresols, isopropylparaben, isopropyl sorbate, lauryl diethylenediaminoglycine HCl, magnesium benzoate, magnesium propionate, methyl-chloroisothiazolinone, methylparaben, octylisothiazolinone, panthenyl ethyl ether benzoate, phenethyl alcohol, phenol, phenoxyethanol, phenoxyethylparaben, phenoxyisopropanol, phenyl benzoate, phenylparaben, o-phenylphenol, polymethoxy bicyclic oxazolidine, potassium benzoate, potassium butylparaben, potassium ethylparaben, potassium methylparaben, potassium paraben, potassium phenoxide, potassium propionate, potassium propylparaben, potassium sorbate, propionic acid, propyl benzoate, propylparaben, quaternium-8 (methyl and stearyl dimethylaminoethyl methacrylate quaternized with dimethyl sulfate), quaternium-14 (ethanaminium, N,N,N-trimethyl-2-[(2-methyl-1-oxo-2-propenyl)oxy]-, methyl sulfate, homopolymer), quaternium-15 (ethanaminium, N,N,N-trimethyl-2-[(2-methyl-1-oxo-2-propenyl)oxy]-chloride, polymer with 2-propenamide), sodium benzoate, sodium butylparaben, sodium p-chloro-m-cresol, sodium dehydroacetate, sodium ethylparaben, sodium formate, sodium hydroxymethane sulfonate, sodium hydroxymethylglycinate, sodium isobutylparaben, sodium isopropylparaben, sodium lauryl diethylenediaminoglycinate, sodium methylparaben, sodium paraben, sodium phenylsulfonate, sodium phenoxide, sodium o-phenylphenate, sodium propionate, sodium propylparaben, sodium sorbate, sorbic acid, TEA-sorbate (triethanolamine sorbate), thianthol (2,7-dimethylthianthrene), triclocarban, triclosan, and undecylenoyl PEG5 paraben (ester of undecylenic acid and PEG5 paraben), and mixtures thereof.

22. A cream according to embodiment 21 wherein the non-formaldehyde-donating preservative is benzoic acid.

23. Use of a composition according to anyone of embodiments 1 to 3 in the treatment or prevention of skin and skin structure infections in a human or an animal.

24. Use of an ointment according to anyone of embodiments 4 and 5 in the treatment or prevention of skin and skin structure infections in a human or an animal.

25. Use of a cream according to anyone of embodiments 6 to 22 in the treatment or prevention of skin and skin structure infections in a human or an animal.

26. Use of anyone of embodiments 23 to 25 wherein skin and skin structure infections are impetigo, foliculitis, furunculosis, acne, secondarily-infected traumatic lesions, overinfected dermatoses, and secondarily-infected burns, and those skin and skin structure infections caused by methicillin-susceptible *Staphylococcus aureus* (MSSA), methicillin-resistant *Staphylococcus aureus* (MRSA) including ciprofloxacin-resistant strains, methicillin-susceptible *Staphylococcus epidermidis* (MSSE), methicillin-resistant *Staphylococcus epidermidis* (MRSE), *Streptococcus pyogenes*, and Group G Streptococci.

27. Use of a composition according to anyone of embodiments 1 to 3 in the treatment or prevention of sexually transmitted diseases and genital tract infections in a human or an animal.

28. Use of an ointment according to anyone of embodiments 4 and 5 in the treatment or prevention of sexually transmitted diseases and genital tract infections in a human or an animal.

29. Use of a cream according to anyone of embodiments 6 to 22 in the treatment or prevention of sexually transmitted diseases and genital tract infections in a human or an animal.

30. Use of anyone of embodiments 27 to 29 wherein the sexually transmitted diseases and genital tract infections are caused by *Streptococcus agalactiae* group B, *Neisseria gonorrhoeae, Chlamydia trachomatis, Mycoplasma hominis*, and *Ureaplasma urealyticum*.

31. Use of a composition according to anyone of embodiments 1 to 3 in the eradication of nasopharynx infections in asymptomatic nasal carriers in a human or an animal.

32. Use of an ointment according to anyone of embodiments 4 and 5 in the eradication of nasopharynx infections in asymptomatic nasal carriers in a human or an animal.

33. Use of a cream according to anyone of embodiments 6 to 22 in the eradication of nasopharynx infections in asymptomatic nasal carriers in a human or an animal.

34. Use of anyone of embodiments 31 to 33 wherein the nasopharynx infections are caused by methicillin-susceptible *Staphylococcus aureus* (MSSA), methicillin-resistant *Staphylococcus aureus* (MRSA) including ciprofloxacin-resistant strains, penicillin-resistant *Streptococcus pneumoniae*, Beta-lactamase positive *Haemophilus influenzae*, non-typeable strains of *Haemophilus influenzae*, Beta-lactamase positive *Moraxella catarrhalis, Neisseria meningitides, Legionella pneumophila, Mycoplasma pneumoniae, Legionella pneumophila,* and *Mycobacterium tuberculosis.*

The invention claimed is:

1. A method of treatment of skin and skin structure bacterial infections caused by *S. aureus* or *S. pyogenes* comprising:
   administering a stable topical cream composition to a subject in need thereof, said stable composition comprising:
   a) 0.2-5% of ozenoxacin, and
   b) a suitable carrier comprising:
   b.1) 15-25% of one or more emulsifiers selected from the group consisting of ethylene glycol monostearate, sorbitan tristearate, a mixture of PEG6 stearate, glycol stearate and PEG32 stearate, and hydrogenated lecithin, and mixtures thereof;
   b.2) 10-20% of one or more surfactants selected from the group consisting of sorbitan oleate monoolein/propylene glycol, $C_8C_{10}$ fatty acid mono- and diglycerides from coconut oil, soy lecithin, egg phosphatides, citric acid esters of monoglycerides, lactic acid esters of monoglycerides, diacetyl tartaric acid esters of monoglycerides, succinic acid esters of monoglycerides, sucrose fatty acid esters, polyglycolyzed glycerides of oleic acids, polyglycolyzed glycerides of linoleic acid, polyglycerol esters of fatty acids, and polyglyceryl esters of mixed fatty acids, and mixtures thereof;
   b.3) 5-15% of an oil component which is the Guerbet alcohol 2-octyl dodecanol;
   b.4) 1-10% of one or more low melting point waxes selected from the group consisting of fatty alcohols having 8 to 30 carbon atoms and mixtures thereof;
   b.5) water;
   b.6) 10-20% of one or more water dispersible components selected from the group consisting of polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide, and mixtures thereof; and
   b.7) 0.01-1% of one or more non-formaldehyde-donating preservatives;
   wherein the amount of component b.5 is an amount to complete 100 percent by weight and all percentages being weight percent and based on the total weight of the composition.

2. The method of treatment of skin and skin structure infections according to claim 1, wherein the skin and skin structure infection is impetigo.

* * * * *